United States Patent
Zombo et al.

(10) Patent No.: US 7,690,840 B2
(45) Date of Patent: Apr. 6, 2010

(54) METHOD AND APPARATUS FOR MEASURING ON-LINE FAILURE OF TURBINE THERMAL BARRIER COATINGS

(75) Inventors: Paul J. Zombo, Cocoa, FL (US); Dennis Lemieux, Casselberry, FL (US); Evangelos Diatzikis, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 970 days.

(21) Appl. No.: 10/610,214

(22) Filed: Jun. 30, 2003

(65) Prior Publication Data

US 2009/0312956 A1  Dec. 17, 2009

Related U.S. Application Data

(63) Continuation-in-part of application No. 09/470,123, filed on Dec. 22, 1999, now abandoned.

(51) Int. Cl.
- *G01N 25/72* (2006.01)
- *G01K 13/00* (2006.01)
- *G01J 5/00* (2006.01)
- *G01N 17/00* (2006.01)

(52) U.S. Cl. .................. 374/121; 374/4; 374/57; 374/144; 250/338.1

(58) Field of Classification Search .......... 374/4–7, 374/120–121, 124, 144, 141, 57; 415/118; 250/338.1; 702/40; 378/58; 73/592; 252/960
See application file for complete search history.

(56) References Cited

U.S. PATENT DOCUMENTS

| | | | | |
|---|---|---|---|---|
| 4,227,369 A | * | 10/1980 | Williams | 60/734 |
| 4,343,182 A | * | 8/1982 | Pompei | 374/31 |
| 4,556,328 A | * | 12/1985 | Orpet | 374/144 |
| 4,582,426 A | * | 4/1986 | Douglas | 356/43 |
| 4,647,220 A | * | 3/1987 | Adams et al. | 374/5 |
| 4,756,752 A | * | 7/1988 | Barnard | 75/230 |
| 4,764,025 A | | 8/1988 | Jensen | |
| 4,765,752 A | | 8/1988 | Beynon et al. | |
| 4,767,937 A | * | 8/1988 | Norsworthy | 348/294 |
| 4,818,118 A | * | 4/1989 | Bantel et al. | 374/7 |
| 4,902,139 A | * | 2/1990 | Adiutori | 374/137 |
| 5,027,268 A | | 6/1991 | Sakurai et al. | |
| 5,111,046 A | | 5/1992 | Bantel | |
| 5,180,285 A | | 1/1993 | Lau | |

(Continued)

FOREIGN PATENT DOCUMENTS

DE  2250142  10/1972

(Continued)

OTHER PUBLICATIONS

Anonymous; "Infrared Scanner Detects Coating Defects," Materials Engineering, vol. 97, No. 10, Oct. 1983, p. 24; XP002161401.

*Primary Examiner*—Gail Verbitsky (57) ABSTRACT

A method of remotely monitoring the radiant energy (6) emitted from a turbine component such as a turbine blade (1) having a low-reflective surface coating (3) which may be undergoing potential degradation is used to determine whether erosion, spallation, delamination, or the like, of the coating (3) is occurring.

28 Claims, 3 Drawing Sheets

U.S. PATENT DOCUMENTS

| | | | |
|---|---|---|---|
| 5,212,099 A * | 5/1993 | Marcus | 436/172 |
| 5,265,036 A | 11/1993 | Suarez-Gonzalez et al. | |
| 5,272,340 A | 12/1993 | Anbar | |
| 5,287,183 A * | 2/1994 | Thomas et al. | 348/571 |
| 5,294,198 A | 3/1994 | Schlagheck | |
| 5,306,088 A | 4/1994 | Zoerner | |
| 5,319,963 A | 6/1994 | Benford | |
| 5,426,506 A | 6/1995 | Ellingson et al. | |
| 5,447,059 A | 9/1995 | Miller et al. | |
| 5,507,576 A | 4/1996 | Fally | |
| 5,552,711 A | 9/1996 | Deegan et al. | |
| 5,562,998 A | 10/1996 | Strangman | |
| 5,582,485 A * | 12/1996 | Lesniak | 374/5 |
| 5,608,845 A | 3/1997 | Ohtsuka et al. | |
| 5,625,153 A | 4/1997 | Sawai et al. | |
| 5,683,825 A | 11/1997 | Bruce et al. | |
| 5,716,720 A | 2/1998 | Murphy | |
| 5,748,500 A | 5/1998 | Quentin et al. | |
| 5,755,510 A * | 5/1998 | Hernandez et al. | 374/121 |
| 5,822,222 A | 10/1998 | Kaplinsky et al. | |
| 5,832,421 A | 11/1998 | Santoso et al. | |
| 5,838,588 A | 11/1998 | Santoso et al. | |
| 5,865,598 A | 2/1999 | Twerdochlib | |
| 6,015,630 A | 1/2000 | Padture et al. | |
| 6,062,811 A | 5/2000 | Zombo et al. | |
| 6,072,568 A | 6/2000 | Paton et al. | |
| 6,109,783 A | 8/2000 | Dobler et al. | |
| 6,153,889 A | 11/2000 | Jones | |
| 6,285,449 B1 | 9/2001 | Ellingson et al. | |
| 6,303,411 B1 * | 10/2001 | Camm et al. | 438/149 |
| 6,346,704 B2 * | 2/2002 | Kenway | 250/341.6 |
| 6,364,524 B1 * | 4/2002 | Markham | 374/131 |
| 6,367,968 B1 | 4/2002 | Ringermacher et al. | |
| 6,394,646 B1 * | 5/2002 | Ringermacher et al. | 374/7 |
| 6,422,741 B2 * | 7/2002 | Murphy et al. | 374/5 |
| 6,422,743 B1 * | 7/2002 | Nirmalan et al. | 374/43 |
| 6,437,334 B1 * | 8/2002 | Thomas et al. | 250/341.6 |
| 6,461,035 B2 * | 10/2002 | Meinlschmidt et al. | 374/5 |
| 6,480,225 B1 * | 11/2002 | Kim | 348/143 |
| 6,563,582 B1 | 5/2003 | Chun | 356/364 |
| 6,690,016 B1 * | 2/2004 | Watkins et al. | 250/341.7 |
| 6,750,454 B2 * | 6/2004 | Brown et al. | 250/341.6 |
| 6,751,342 B2 * | 6/2004 | Shepard | 382/141 |
| 6,796,709 B2 * | 9/2004 | Choi | 374/102 |
| 2001/0005392 A1 * | 6/2001 | Schutz et al. | 374/5 |
| 2003/0128736 A1 * | 7/2003 | Dalio et al. | 374/141 |
| 2005/0063450 A1 * | 3/2005 | Willsch et al. | 374/57 |

FOREIGN PATENT DOCUMENTS

| | | |
|---|---|---|
| DE | 19720461 A1 | 2/1998 |
| EP | 0618432 A2 | 10/1994 |
| EP | 0898158 A2 | 2/1999 |
| GB | 1480347 | 7/1977 |
| GB | 2164147 A | 3/1986 |
| GB | 2313189 A | 11/1997 |
| JP | 61172059 A * | 8/1986 |
| JP | 61265569 A * | 11/1986 |
| JP | 2003098134 A * | 4/2003 |
| WO | WO 9954692 A | 10/1999 |

\* cited by examiner

METHOD AND APPARATUS FOR MEASURING ON-LINE FAILURE OF TURBINE THERMAL BARRIER COATINGS

This application is a Continuation-In-Part of U.S. application Ser. No. 09/470,123 filed Dec. 22, 1999 now abandoned.

GOVERNMENT CONTRACT

The Government of the United States of America has rights in this invention pursuant to Contract DE-AC05-95OR22242 awarded by the United States Department of Energy.

BACKGROUND OF THE INVENTION

1. Field of the Invention

The invention relates to means to identify, monitor and take action upon potential delamination of ceramic coatings used as a thermal barrier for turbine components.

2. Background Information

Cobalt or nickel based superalloys of, for example, IN738, or ECV768 are used for making blades, vanes and other components of gas turbines. These turbines can operate at temperatures in the range of 1000 C. to 1600 C. and are generally protected by a series of protective coatings. The coatings usually comprise layers of metallic base coats, service formed aluminum oxide layers and a final ceramic thermal barrier coating ("TBC"). The TBC is usually made of yttria, ceria or scandia stabilized zirconia, as taught, for example, by U.S. Pat. Nos. 5,180,285; 5,562,998; 5,683,825 and 5,716,720 (Lau, Strangman, Bruce et al., and Murphy, respectively). Long term exposure of these ceramic coatings to the hostile, high temperature, abrasive environment in which such turbines operate can cause phase destabilization, sintering, microcracking, delamination and ultimately spallation within the coating layers, exposing the superalloy component to degradation or failure and requiring expensive repairs.

Many attempts have been made to non-destructively test such coated superalloy metal surfaces for non-obvious, sub-coating degradation. U.S. Pat. No. 4,647,220 (Adams et al.) teach a system to detect corrosion and stress corrosion cracking of painted metal structures, utilizing infrared thermographic techniques to detect temperature differentials caused by the difference in thermal conductives between corroded metal and uncorroded metal. A scanner can be used to produce a television-compatible, video output signal of the thermophysical characteristics it is viewing. This system is used primarily on stationary military aircraft. U.S. Pat. No. 5,294,198 (Schlagheck) teaches a system to determine defects in commercial products by obtaining an infrared image of the product while it is being stimulated. An infrared television monitor supplies a signal to a color monitor where hot or cold temperature regions appear as red or blue respectively. Defects can be determined by an inspector or a computer. This system can also be incorporated into production lines, and eliminates prolonged vibration and/or temperature cycling as tests of commercial products.

In U.S. Pat. No. 5,272,340 (Anbar) teaches an infrared imaging system which simultaneously generates temperature, emissivity and fluorescence, for use in clinical diagnosis and management of skin disorders, to determine true skin temperature as a tool in the treatment of malignancies, burns and the like. U.S. Pat. No. 5,608,845 (Ohtsuka et al.) relates to predicting the remaining lifetime, by parts degradation analysis, of, for example, carbon seals, electrically operated values, control rod drivers, and the like, in locations such as electric power plants. This appears to be accomplished by establishing a series of lifetimes based on experimental aging degradation data.

In U.S. Pat. No. 5,552,711 (Deegan et al.), probable turbine blade failure is determined by measuring specific ions emitted by hot spots. The invention relates to electromagnetic energy radiated by ions that are created as combustion gas erodes and ionizes materials in these hot spots using spectral detectors looking for characteristic ions. However, this system requires failure to occur, for example by melting of components and detection of ions. Turbine blade temperature monitors are taught by U.S. Pat. No. 5,306,088 and 5,832,421 (Zoerner and Santoso et al., respectively). Zoerner requires an actual fiber-optical cable actually disposed inside a turbine component. Santoso et al. require measurement of pressure and temperature at locations other than the blades and then simulating blade temperature values using a water stream cycle analysis program and then training an artificial network so that it can learn to recognize a failure by estimating blade temperature.

In U.S. Pat. No. 4,764,025 (Jensen), a temperature detection pyrometer is used to determine turbine blade temperature from radiation reflected and emitted from the blade. The system substantially reduces the effect of reflected radiation from flame or hot carbon particles. Detected radiation is divided into two channels and the output of one of the detectors is weighted relative to the other. The difference between the factored output from one detector and the output from the other detector is provided to a difference amplifier to provide a signal directly related to the temperature of the turbine blade.

There is still special need, however, to be able to sense potential failure situations for complex, moving turbine components having ceramic coating layers, by utilizing a very fast sensor system. This would require measuring relative spatial/time radiance using an expert system, and some sort of a degradation model that will generate advisory information and actively avert failure. This system must identify very small hot spots on low-IR emittance ceramic surfaces, detect spalling and debond areas, measure their growth, and forecast and prevent failure.

SUMMARY OF THE INVENTION

Generally, the present invention fulfills the foregoing needs by providing in one aspect thereof a method and apparatus effective to monitor delamination of cooled, low-IR emittance ceramic turbine components which may be in a hostile environment and moving at Mach speeds, so that detection of debond areas or the like within the ceramic, or separate cooling system failures, triggers almost instantaneous means, e.g., within approximately 5-10 seconds delay, to analyze potential damage and shut down the apparatus if necessary.

The present invention further fulfills the foregoing needs by providing a method for monitoring a cooled, operating turbine component which will contain an exterior protective ceramic thermal barrier coating undergoing potential degradation in a corrosive, high temperature turbine environment and having a low-IR emittance surface, by remote monitoring of radiant energy, to determine any degradation of the cooling system, and/or of the thermal barrier coating, caused by at least one of erosion, corrosion, sintering, microcracking, spallation and bond delamination; having a database means evaluate said degradation; and optionally modifying the operating parameters of the turbine based on the evaluation of the degradation.

Additional aspects of the invention may also reside in a method for generating data from non-destructive monitoring of a turbine component, which is contacted by a cooling medium and which will contain an exterior protective ceramic thermal barrier coating undergoing potential degradation in a corrosive, high temperature turbine environment, by (A) providing an infrared thermal imaging device; (B) providing a data base connected to the imaging device to provide a measuring system, the measuring system having at least one sensor effective to quantitatively measure and generate data by using non-destructive, remote monitoring of the surface radiance distribution, without physical contact of the thermal barrier coating, directly at the surface of the thermal barrier coating where such distributions are caused by heat flow within the thermal barrier coating; (C) monitoring the radiance of the measuring system to determine any degradation of the cooling system, or of the thermal barrier coating, caused by at least one of erosion, corrosion, sintering, microcracking, spallation, and bond delamination; (D) having the database evaluate said degradation; and (E) optionally modifying the operating parameters of the turbine based on the evaluation of the degradation. The turbine component is cooled or contacted by a cooling medium supplied by an associated cooling system, as is well known in the prior art. By "data" is meant: a spatial, registered map of surface radiance of key surfaces of turbine blades. Data may be stored and new data may be continually compared for spatial differences. By "radiance" is meant: Radiant power per unit source area per unit solid angle expressed in watts/$m^2$/steradian. By "evaluate" is meant: to review data for significant events.

Further aspects of the invention may also reside in an apparatus for non-destructive inspection of a moving turbine component contacted by a cooling medium which component has an exterior ceramic thermal barrier coating undergoing potential degradation in a corrosive, high temperature environment, the apparatus comprising: (I) a measuring system comprising: (A) an infrared thermal imaging device, and (B) a database connected to the imaging device, said measuring system being effective to remotely measure and generate data based on the radiance distribution of the moving turbine component without physical contact to detect degradation of the ceramic coating, (II) a database effective to evaluate said degradation and forecast remaining life as determined by an expert system, (III) a module configured to modify the operating parameters of the turbine based on the evaluation of the degradation, (IV) a module configured to hypothetically (virtual space) adjust operating parameters to optimize remaining life, and (V) an expert system to determine the optimal operating parameters to maximize life for a given performance need. Preferably, the TBC has a low-IR emittance surface and thus mostly radiant energy rather than contra-informational reflected energy will be measured. Aspects of this invention not just allow for the detection of debond, but the ability to watch the debond grow and the ability to known when the debond spalls so that the turbine can be shut down.

Recent increases in the efficiencies required of land-based combustion turbine engines have not only mandated the use of TBCs on blades and vanes, but, also have made the survivability of these coatings a critical factor in the continuing operation of the turbine. The ability to monitor the structure and status of blade and vane coatings will provide the day-to-day capability to operate the turbine at maximum efficiency and will provide for the timely warning of on-setting or on-going failures, and thereby help avoid the severe repair and maintenance costs that would be incurred by catastrophic vane or blade failures. Today, the U.S. demand for new electrical generating capacity is 13,000 MW per yr. and gas turbines are playing an increasingly important role in meeting this demand in a clean, efficient, reliable manner. Combustion turbine technology is rapidly evolving, and the need to insert new technology is critical to remain competitive in the global market. The development of an on-line TBC monitor is a crucial technology for advanced turbines.

An effective on-line TBC monitor system would have the following major economic benefits: accelerate the sale of advanced power plants that use advanced turbine engines; improve the reliability of advanced turbine engines by the early identification of the need for TBC maintenance; and accelerate the adoption of advanced upgrade packages to existing turbine engines that can improve plant efficiency; thereby, lowering the cost of electricity.

Some of the novel features of the invention may include: (a) thermal imaging for the examination of TBC coated components in motion at Mach speeds, (b) the ability to conduct quantitative measurements non-destructively, (c) the ability to conduct these measurements without contacting the component from relatively large distances, (d) the ability to conduct limited measurements without interrupting or with minimal interruption of the operation of the engine, and (e) the ability to make immediate operating decisions in order to minimize risk and damage due to TBC failure. This system could also be used off-line, and would allow nondestructive and noncontact quantitative measurements, for new, service exposed, and service exposed repaired components of: unbonds, thickness, and intrinsic and extrinsic thermal properties while the components are available for direct handling. An off-line remote system would allow remote thermal imaging of critical turbine components with little or no disassembly.

BRIEF DESCRIPTION OF THE DRAWINGS

The above and other advantages of this invention will be more apparent from the following description in view of the drawings in which.

DETAILED DESCRIPTION OF THE INVENTION

Aspects of this invention will provide a means of examining TBC coatings at various stages during the life cycle of the component. In the on-line system, this invention would allow notification within several seconds of debonding and spallation and cooling system failure during the uninterrupted operation of the turbine engine. Furthermore, by tracking the surface temperature in time, long term degradation mechanisms, such as erosion and sintering can be evaluated. This is of key importance with new engine designs where eminent engine failure could occur within minutes of a coating failure.

In one exemplary embodiment, a system embodying aspects of the present invention will be configured to measure the radiance of a moving turbine blade in a gas turbine under operating conditions. The blades may be moving at supersonic linear speeds in the order of approximately Mach 1.2 or 890 miles per hour. Surface temperature of the TBC for a turbine blade under normal operating conditions may be in the order of approximately 1340 degrees Celsius. The system will monitor, in near real-time (e.g., in a range of approximately 5-10 seconds), during engine operation, the formation and progression of potentially critical TBC defects. The system will track the progression of TBC defects, estimate TBC remaining life and notify operations of blade conditions, oversee and report on component status and recommend best operating practices.

Unlike pyrometer systems that commonly use a single point of the desired surface to measure temperature, a system embodying aspects of the present invention would preferably use a focal plane array sensor (e.g., an array of charged coupled devices (CCD)) to measure the emitted radiance of the entire area of the surface to be measured.

Based on studies of the emittance within an IR bandwidth ranging from about 0.9 µm to about 14 µm, we have determined that at the longer wavelengths, e.g., from about 8 µm to about 14 µm, within the IR bandwidth, we observe higher levels of emittance, and at the shorter wavelengths, e.g., ranging from about 0.9 µm to about 5 µm within the IR band we observe relatively less emittance.

Aspects of the invention may use thermal imaging cameras to detect failure of the cooling system used to cool operating turbine components and debonding of coating systems. An external IR source may be used to initiate a thermal transient for any off-line embodiment. The internal cooling of the blade provides the heat transient for the on-line embodiment. As the heat is conducted through the coating and into the substrate material, the radiance of the local surface is affected. The term "radiance" is hereby defined as the total emittance, in this case, total reflective thermal emittance, from the surface of an object. Emittance is synonymous with radiance, that is, radiant energy emitted by a free surface. Infrared is the region of the electromagnetic spectrum between microwave and visible light. Reflected is electromagnetic energy that undergoes a redirection, with no change in energy upon interaction with a free surface.

Local surfaces of debonded areas exhibit a distinctly different radiance than that of bonded areas because they have a different emittance. Low emittance surfaces will appear cooler than the surrounding bonded surfaces due to their lower radiance. And by similar principles, coating material thickness, thermal conductivity, heat capacity and emissivity will also affect the surface radiance. These effects can therefore be measured and related to the condition of the coating on the component. Preferably, the TBC will have a "low-IR emittance surface" so that radiance is predominant and monitored by an infrared camera leading to more accurate representations of real defect features. The low-IR emittance surfaces usually can be zirconia based TBCs, but can also be zirconia stabilized with transition metal oxides; yttria, scandia, ceria and magnesia stabilized oxides; yttria stabilized zirconia, ceria stabilized zirconia, scandia stabilized zirconia; or non-zirconia based TBC.

Figure 1:
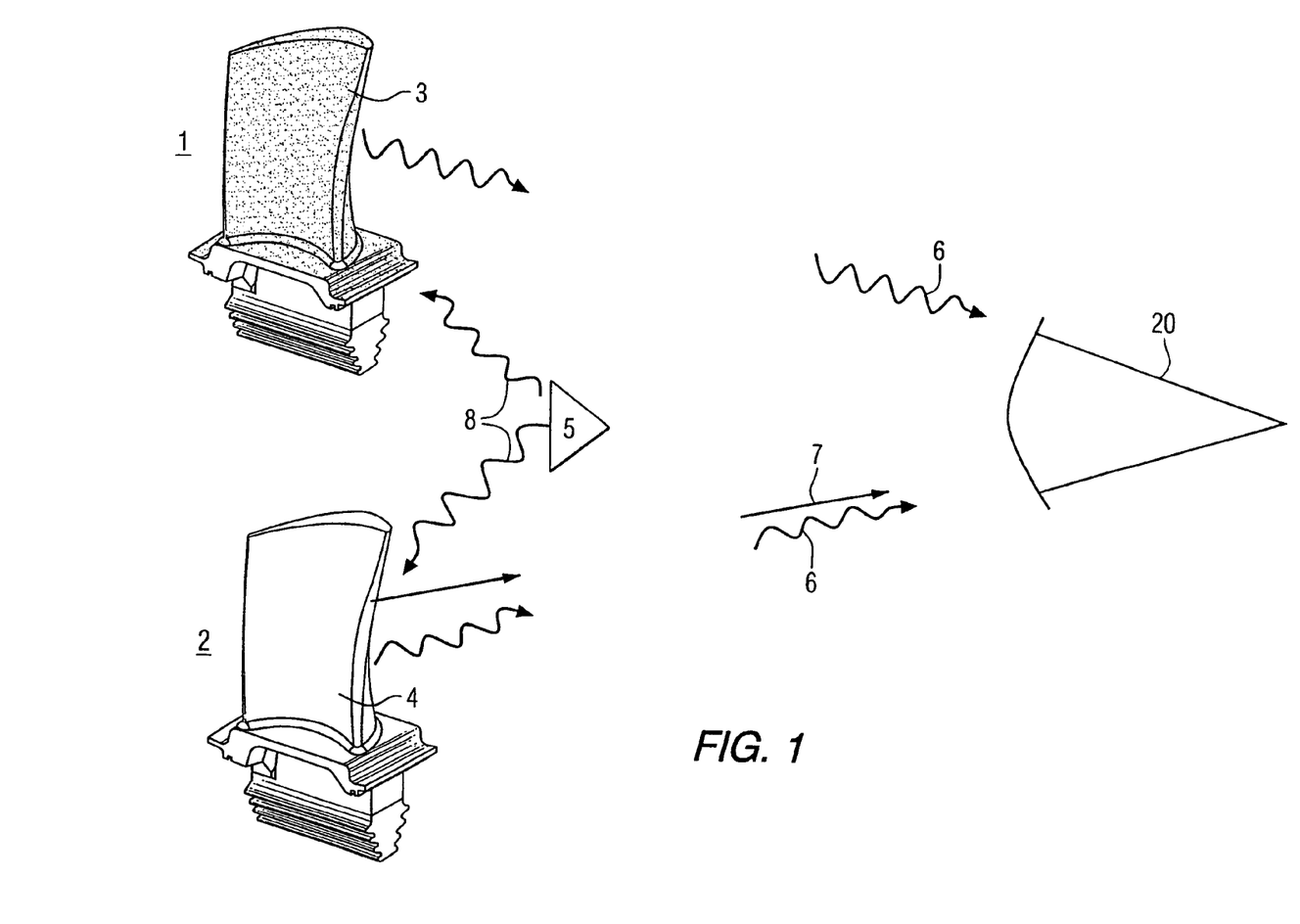
FIG. 1, is an enlarged view of two turbine blades absorbing heat from a heat source and radiating/reflecting energy to an infrared thermal imaging camera associated with the remote monitoring means of this invention.

When trying to observe a component's radiant thermal energy, if the component is highly reflective, a problem can occur that will result in misreadings. Reflected thermal energy from other objects of higher temperatures can make the object of interest look hotter. An optical light analogy would be to ask ourselves: "what is the color of a mirror." The answer depends on the color of the object being reflected off the mirror. This observation/misreading problem does not happen with low-reflective surfaces. In the low-reflective case, the observed radiant energy is predominantly characteristic of the surface of interest. To better illustrate this point and facilitate understanding of the term "low-IR emittance" refer now to FIG. 1 which shows three components: turbine blade 1 with low reflectance TBC coating 3, turbine blade 2 with high reflectance metallic coating 4, both at 1200° C., and an upstream component 5 that is hotter than 1 or 2 at 1350° C. The hotter component 5 radiates thermal energy 8 that is indicative of the component temperature. This energy can reflect off reflective surface 4 of blade 2 but not off the non-reflective surface 3 of blade 1.

For one exemplary on-line embodiment, the components are periodically thermally imaged, and differences of surface radiance are noted and tracked in near real-time operation of the component. Additionally, rapid analysis and decision systems utilizing both expert and supervisory subsystems would be employed to summarize data and make decisions regarding the operation of the turbine. The expert systems would include TBC life and debond growth algorithms that would forecast the operating time available once a debond is detected. The expert system would be interactive to allow the operator or a computer to change turbine operation conditions in virtual space and generate estimates of remaining life of the TBC system.

Figures 2, 3:
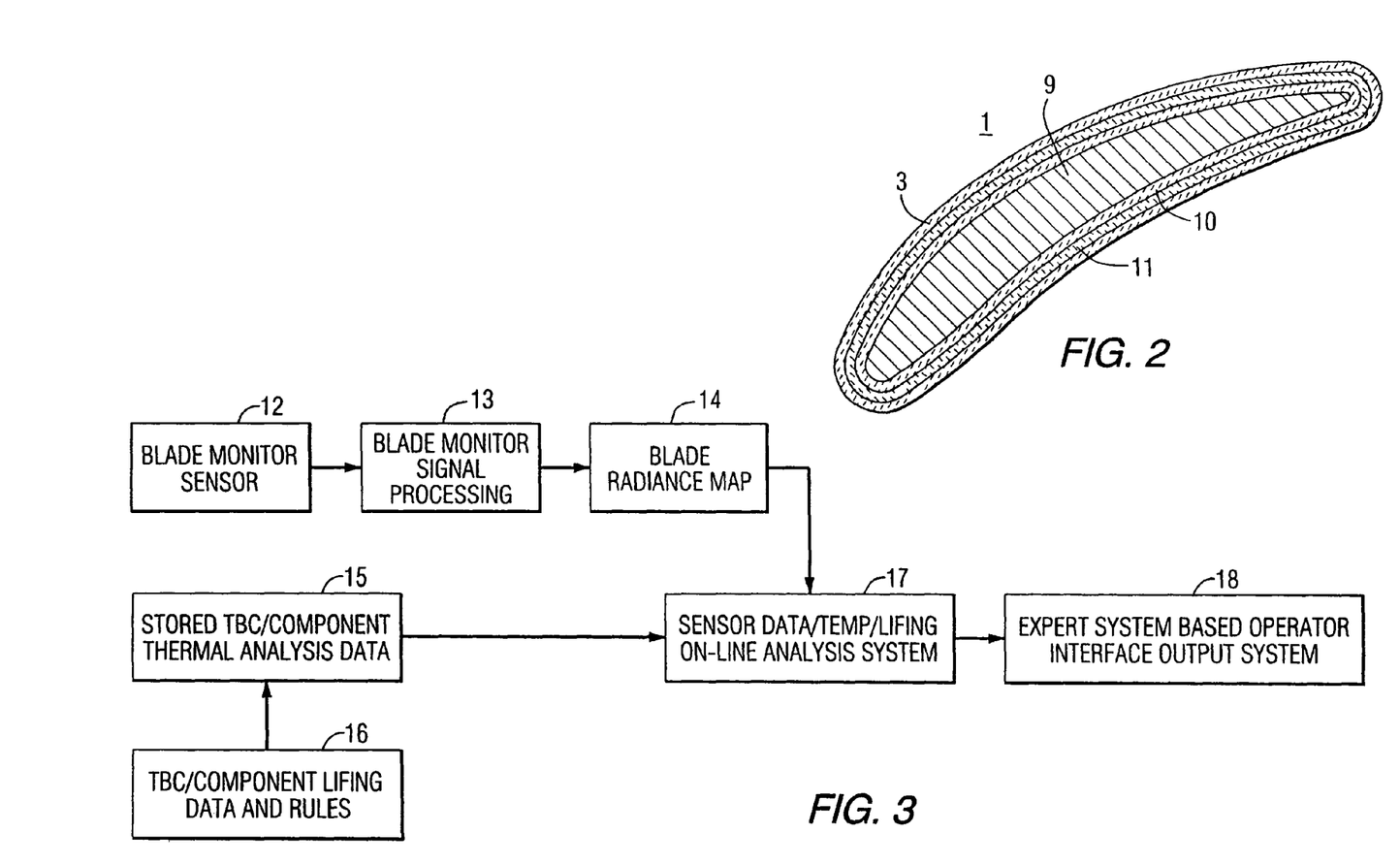
FIG. 2 is an enlarged cross-section of a typical turbine blade.
FIG. 3 is a block diagram of one method of this invention.

Aspects of this invention propose to address the development of an on-line coating monitor system for TBCs by developing blade and vane monitoring systems and integrating them into a computerized high-speed analysis system that can be installed on an operating turbine. FIG. 3 depicts an exemplary proposed implementation of this concept. The method may start with developing a clear understanding of the required system capabilities and a correlation with prospective sensor capabilities. The speed capabilities of sensor and computer analysis systems will also be evaluated. One exemplary embodiment is based upon a focal plane array that will monitor blades as they pass by a vantage viewing area.

The blade measuring/monitoring system includes sensor 12, signal processor 13, and radiance map or means 14, and will be based upon modification to existing infrared imaging technology.

This technology is able to acquire thermal images at sufficient speed and resolution to monitor high-speed events such as the motion of a turbine blade past a viewing port at linear speeds of approximately up to Mach 1.2 or 890 miles per hour. It is not necessary to view and acquire images of every blade every time it passes the camera, but it is necessary to acquire a single blade image over a short time interval. Calculations have shown that in order to obtain the resolution needed from a moving blade at Mach 1.2 speeds, the focal plane array camera should be able to integrate the IR signal within 3 microseconds or less. Otherwise, spatial distortions may render the image essentially useless. Data should be acquired for all blades and then correlated with previous images of each of the blades. Long term changes would be realized by comparison of current images with older archived images.

The sensor system is configured to provide useful data in real time, and the analytical model is configured to predict component performance. One key element of the computer system will be a storage and retrieval system that will compare on-line data for the assessment of the coating condition. Digital IR images for each blade in a row can be easily accessed and stored using frame grabbers and modern computer workstations. Only the actual hardware remains to be configured and software must be developed. Also included in the system is the stored TBC/component thermal analysis database 15. TBC/component life database 16, sensor data/temperature/life on-line analysis system 17 and an expert system based operator interface output system 18. Thermal analysis database 15 may comprise up-to-date spatial data of radiance for each blade or vane. Component life database 16 may comprise historical spatial data of radiance for each blade or vane. Sensor/data/temperature/life on-line analysis system 17 may comprise a system that compares current data with historical data to look for evidence of TBC failure. Expert system 18 may comprise a system that takes evidence of failure and tests against operating conditions, determines relevance, and estimates remaining life.

Figure 4:
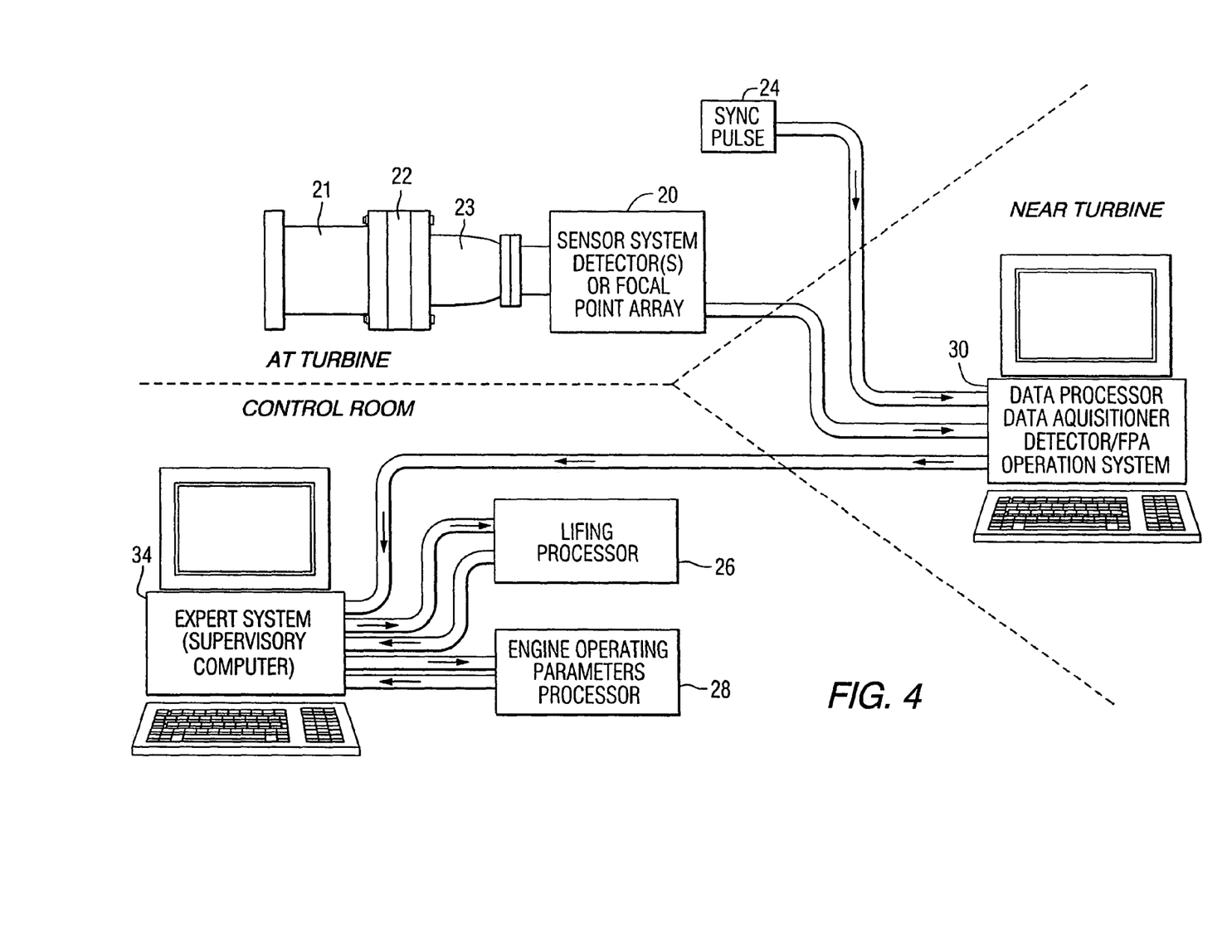
FIG. 4 is a schematic digram of a blade monitor system utilizing this invention.

The computer analysis and operator interface will be a dual-level hierarchical system shown in FIG. 4. At the lower level, dedicated sensor computers 30 will monitor on-line sensor 20, an RPM sensor and per rev signal 24. The IR port 21 will provide a direct "line of sight" to the blade path. Pressure barrier 22 will allow IR signal through to sensor system 20. Optical system 23 will allow focal length adjustment for necessary magnification. At the higher level, a supervisory computer 34 containing an advisory expert system will oversee the sensor computers 30. This supervisory system will contain knowledge that will identify an impending failure and prescribe corrective action. The supervisory computer may have at least two subsystems: a life processor 26 which determines remaining life of TBC, damage and an engine operating parameter processor 28 which continually monitors engine parameters like: temperature, speed, fuel consumption and power output.

Infrared transmission, absorption, and emissivity properties of the turbine engine gas will be initially calibrated within the range of operating parameters expected. Thermal emission characteristics will be determined for several "states" of the TBC condition. The characteristics will include emissivity, conductivity, and absorption as a function of temperature and wavelength. Normal changes of the TBC including sintering and contamination will be taken into account. Characteristics of deteriorating TBCs will be studied and compared to normal changes in the undeteriorated state. TBCs are subject to sintering and innocuous contamination, both of which are expected to influence measured spectral properties. Also, because aspects of the present invention have innovatively discovered that TBCs tend to exhibit a transparent nature at the shorter wavelengths, e.g., within an IR bandwidth ranging from about 0.9 µm to about 5 µm, that are expected to be employed in the sensor system. The thermally grown oxide (TGO) that continually grows between the TBC and the bond coat is also expected to affect the spectral properties. These properties may be exploited to selectively monitor emissions originating from under the TBC, i.e., emissions that may indicate a condition of interest related to the TGO layer, the bond coat layer or the underlying metal substrate material. These normal changes are gradual, and therefore, are expected to cause gradual and accountable changes in the emission of a normal TBC. The expert system will learn to compensate for these changes.

In one aspect of the invention a focal plane array imaging sensor may be configured to sense an IR signal in a selectable bandwidth. The selection of the bandwidth may be made to enhance the detectability of perturbations that may occur within a specific layer neighboring the ceramic coating. For example, an IR bandwidth ranging from about 0.9 µm to about 5 µm would essentially make the ceramic coating transparent to an IR signal passing therethrough notwithstanding the presence of a specific layer of TGO. This is advantageous because this would allow monitoring precursor conditions that, if left uncorrected, would eventually result in spallation of the TBC. An example of such a precursor condition may be debonding at the TGO-to-TBC interface. Such debonding would cause a change in the IR signal in the 0.9 µm to 5 µm range, and such signal would pass through the TBC which is transparent in this range.

Deteriorating TBC will cause a local step change in radiance. Two primary deterioration conditions may be: debonding at the TGO-to-TBC interface, and final spallation of the TBC. The debonding will be the precursor to most spallations, the exception being those caused by foreign object impact damage. The temperature of the unattached TBC region will increase as the debond grows, and the IR imaged area will also grow. At some critical size, the debonded region will spall off, exposing the cooler bond coat surface to the hot turbine engine gas, and a local drop in radiance will be apparent.

Critical hot section components are commonly cooled by using cooling gases, pumped from an associated cooling system, that travel through specific passages within the component. If the passages become ineffective for reasons like blockages, wall failure or oxidation, the component life will be diminished. Because of the concern for the failure of the cooling system, the invention described herein is also needed to monitor surface radiance changes that are directly a result of cooling system failures.

The supervisory software 34 for the whole design will store all the processed data coming from the blade through sensor 20 and the on-line temperature and life analysis systems. The data will be supplemented by common engine operating parameters.

Data will be processed into a meaningful form to demonstrate changes or excursions that require reporting to the control software. The control software will interpret the reported trends or excursions and notify or alert the operator of the finding. Different types of preprocessing logic will be used to identify excursions or trends. Raw data signals will be processed as collected. Some preprocessing steps will include a continually updated running average with statistical significance for ongoing data collection. This will establish a baseline for comparison of each refreshed data set. Excursions from this baseline will be brought to the attention and disposition of the expert system. Historical averages will be periodically stored for long-term trending and supervisory system disposition. The system will report information in the following categories: temperature maps, remaining life of TBC, recommendations for optimizing specific operating parameters, and emergency alert. By continually monitoring the operating conditions, the remaining life for different future operating conditions will be forecasted. The operator will have the ability to balance power output and TBC life expense rate based on advice given by the control system software. This will optimize power output and outage scheduling for maximum operator control. The system will provide alarms for critical TBC loss situations. The alarms will notify operators only in the event of eminent damage or failure. The system will also provide alarm signal outputs for connection to standard tripping control devices for the option of automatic tripping.

The present invention may be embodied in other forms without departing from the spirit or essential attributes thereof, and accordingly, reference should be made to both the appended claims and the foregoing specification as indicating the scope of the invention.

We claim as our invention:

1. A near real-time method for inspecting a rotationally operating turbine component, the component having an exterior protective ceramic thermal barrier coating potentially undergoing degradation in a corrosive high temperature turbine environment, the component further having a cooling system, the method comprising:

remotely monitoring radiant energy from an area of the turbine component while the component is rotating, said monitoring being performed with a focal plane array imaging sensor configured to concurrently acquire a plurality of thermal imaging points spatially registered over said area of the component and having sufficient resolution to identify an incipient degradation of the cooling system and/or the thermal barrier coating prior to said degradation escalating to a point of failure of the component;

processing said plurality of thermal imaging points to generate an image of said area of the turbine component to indicate the incipient degradation in the area of the turbine component; and evaluating the incipient degradation indicated in the image, wherein said monitoring, processing and evaluating are effected within a sufficiently short period of time to avert an escalation of said incipient degradation to the point of failure of the turbine component.

2. The method of claim 1, where the turbine component is a turbine blade and the thermal barrier coating is zirconia based with a low-IR emittance surface.

3. A near real-time method for generating data from inspection of a rotationally operating turbine component which has an exterior protective ceramic thermal barrier coating potentially undergoing degradation in a corrosive high temperature turbine environment, the method comprising:

(A) providing a plurality of infrared thermal imagers for concurrently acquiring, while the component is rotating, a plurality of spatially registered thermal imaging points over an area of the thermal barrier coating, wherein said plurality of thermal imaging points is used to sense a surface radiance distribution caused by heat flow within the area of the thermal barrier coating;

(B) generating data from the sensed surface radiance distribution, said data having sufficient resolution to identify an incipient degradation in the thermal barrier coating prior to said degradation escalating to a point of failure of the component;

(C) processing the data to generate an image of said area of the coating to indicate the incipient degradation of the thermal barrier coating;

(D) evaluating the incipient degradation indicated in the image; and (E) optionally modifying the operating parameters of the turbine based on the evaluation of the degradation in near real-time, wherein said acquiring, generating, processing, evaluating, and modifying, if any, are effected within a sufficiently short period of time to avert an escalation of said incipient degradation to the point of failure of the turbine component.

4. The method of claim 3, where the thermal barrier coating has a low-IR emittance surface.

5. The method of claim 3, where the thermal barrier coating has a zirconia based low-IR emittance surface so that the remote monitoring is of substantially all radiant energy with little reflective energy.

6. The method of claim 3, where the infrared thermal imagers comprises a plurality of infrared cameras.

7. The method of claim 3, where the data is generated by at least a signal processor and a temperature determiner.

8. The method of claim 3, where the infrared thermal imagers comprises a focal plane array of sensing devices configured to sense an IR bandwidth from about 0.9 µm to about 14 µm.

9. The method of claim 3, where the turbine component is a turbine blade rotating at speeds of from 60 to 3600 revolutions per minute and where the infrared thermal imager acquires a single blade image over a time interval being sufficiently fast relative to the revolutions per minute of the blade.

10. The method of claim 3, where the turbine component is a turbine blade and where the data is acquired for all blades and then correlated with previous images of each blade for evaluating incipient degradation indicated in a present image.

11. The method of claim 3, where an IR radiance map of the surface of the component is continually updated.

12. The method of claim 3, where the surface radiance distribution comprises radiance of wavelengths in an IR bandwidth from about 0.9 µm to about 14 µm to detect local perturbations indicating spallation and bond delamination.

13. The method of claim 12, where the infrared thermal imagers measures the change in radiance of one specific wavelength.

14. The method of claim 3, where the turbine component has a ceramic exterior thermal barrier coating having a low-IR emittance surface in which a reflected component of thermal energy is not significant, and where the thermal barrier coating has a low-IR emittance surface of zirconia stabilized with transition metal oxides.

15. The method of claim 3, where the turbine component has a ceramic exterior thermal barrier coating having a low-IR emittance surface in which a reflected component of thermal energy is not significant, and where the thermal barrier coating has a low-IR emittance surface selected from the group consisting of yttria, scandia, ceria and magnesia stabilized oxides.

16. The method of claim 3, where the turbine component has a ceramic exterior thermal barrier coating having a low-IR emittance surface in which a reflected component of thermal energy is not significant, and where the thermal barrier coating has a low-IR emittance surface selected from the group consisting of yttria, ceria and scandia stabilized zirconia.

17. The method of claim 3, where the turbine component has a ceramic exterior thermal barrier coating having a low-IR emittance surface in which a reflected component of thermal energy is not significant, and where the thermal barrier coating has a low-IR emittance surface of a non-zirconia based material.

18. An apparatus for inspection of a moving turbine component which component has an exterior ceramic thermal barrier coating potentially undergoing degradation in a corrosive high temperature environment, the component further having a cooling system for internally cooling the turbine component, the apparatus comprising:

(I) a near real-time measuring system including a thermal imager comprising a focal plane array imaging sensor that measures a heat transient on the internally cooled moving turbine component, said heat transient measurement comprising a plurality of spatially registered thermal imaging points over an area of the component, said plurality of thermal imaging points being concurrently acquired and having sufficient resolution to identify an incipient degradation of the cooling system and/or of the thermal barrier coating prior to said degradation escalating to a point of failure of the component, said thermal imager operatively connected to a signal processor that generates an image of the area of the component based on the measured heat transient within a few seconds of the measurement and without physically contacting the moving turbine component to detect the incipient degradation of the ceramic coating, and avert an escalation of said incipient degradation to the point of failure of the component; and (II) a computer system operatively connected to the measuring system effective to evaluate the degradation and forecast remaining life and having a supervisory system capable of modifying operating parameters of the turbine based on the evaluation of the degradation and adjusting at least one of the operating parameters to optimize remaining life.

19. The apparatus for inspection of a moving turbine component of claim 18, wherein the computer system also determines optimal operating parameters to maximize life for a given performance need.

20. The method of claim 1, further comprising modifying operating parameters of the turbine based on the evaluation of the degradation.

21. An apparatus for inspection of a turbine component in a high temperature environment, the component comprising a ceramic thermal barrier coating over a substrate, the apparatus comprising:

a thermal imager that measures emissions from the turbine component, wherein the thermal imager comprises a focal plane array imaging sensor configurable to sense emissions based on a plurality of concurrently acquired and spatially registered thermal imaging points over an area of the component, and having sufficient resolution to identify an incipient degradation prior to said degradation escalating to a point of failure of the component, and further wherein the sensor is configurable to sense emissions from at least one of the following: emanating from the ceramic thermal barrier coating; and emanating from below the ceramic thermal barrier coating and passing through said thermal barrier coating; and a signal processor operatively connected to the thermal imager to process said spatially registered thermal imaging points to generate a respective image of the coating and/or below the coating based on the measured emissions to detect the incipient degradation in the coating and/or below the coating of the component and avert an escalation of said incipient degradation to the point of failure of the component.

22. The apparatus of claim 21 further comprising a supervisory system responsive to the signal processor to modify an operating parameter of the turbine.

23. An apparatus for inspection, in a high temperature operational turbine environment, of a turbine component comprising an exterior ceramic thermal barrier coating over a layer neighboring the ceramic thermal barrier coating, the neighboring layer disposed over a substrate, the turbine component further comprising structural features internal to the component, the apparatus comprising:

a near real-time measuring system including a thermal imager that measures a heat transient on the turbine component, wherein the thermal imager comprises a focal plane array imaging sensor configured to concurrently acquire using an IR signal in a selectable bandwidth a plurality of spatially registered thermal imaging points over an area of the component and having sufficient resolution to detect an incipient degradation prior to said degradation escalating to a point of failure of the component, the selection of the bandwidth being made to enhance at least one of the following: detectability of incipient degradation that may occur within the ceramic thermal barrier coating; detectability of incipient degradation that may occur within the layer neighboring the ceramic thermal barrier coating, detectability of incipient degradation in the internal structural features, and detectability of incipient degradation that may occur in the substrate beneath the neighboring layer; and a signal processor operatively connected to the measuring system to process said spatially registered thermal imaging points to generate a respective image to detect the incipient degradation in at least one of the following: incipient degradation that may occur within the ceramic thermal barrier coating; incipient degradation that may occur within the layer neighboring the ceramic thermal barrier coating, incipient degradation in the internal structural features, and incipient degradation that may occur in the substrate beneath the neighboring layer, wherein the detection of the incipient degradation is effected by said processor within a sufficiently short period of time to avert an escalation of said incipient degradation to the point of failure of the turbine component.

24. The apparatus of claim 23 wherein the bandwidth is selected to range from about 0.9 µm to about 5 µm for making the ceramic coating transparent to an IR signal passing there through.

25. An apparatus for inspection, in a high temperature operational turbine environment, of a moving turbine component which component comprises an exterior ceramic thermal barrier coating, the apparatus comprising:

a near real-time measuring system including a thermal imager that measures the heat transient on the turbine component, wherein the infrared thermal imager comprises a focal plane array imaging sensor configured to concurrently acquire using an IR signal having a bandwidth from about 0.9 µm to about 14 µm a plurality of spatially registered thermal imaging points over an area of the component and having sufficient resolution to identify an incipient degradation of the thermal barrier coating prior to said degradation escalating to a point of failure of the component, the imaging sensor further configured with a sufficiently fast integration time to capture imaging data of the area of the component free from distortion for each individual blade in a turbine component rotatable at speeds of up to 1.2 Mach; and a processor configured to process said imaging data to generate an image of said area of the coating to indicate the incipient degradation of the thermal barrier coating, said processor including a module for evaluating the incipient degradation indicated in the image, wherein the heat transient measurement provided by the measuring system, the image processing provided by said processor, and the evaluation provided by said module is effected within a sufficiently short period of time to avert an escalation of said incipient degradation to the point of failure of the turbine component.

26. The apparatus of claim 25 wherein the integration time is within 3 microseconds or less.

27. A method for performing inspection of an internally cooled turbine component which has an exterior ceramic thermal barrier coating in a high temperature environment, the method comprising:

measuring emissions from the internally cooled turbine component with an IR sensor that comprises a focal plane array imaging sensor configured to concurrently acquire a plurality of spatially registered thermal imaging points over an area of the component, and having sufficient resolution to identify an incipient degradation prior to said degradation escalating to a point of failure of the component;

configuring the sensor to sense an IR bandwidth from about 0.9 μm to about 5 μm in order to sense emissions emanating from below and passing through the exterior ceramic thermal barrier coating; and generating an image based on the measured emissions to detect incipient degradation below the exterior ceramic thermal barrier coating, wherein said generating is effected within a sufficiently short period of time to avert an escalation of said incipient degradation to the point of failure of the turbine component.

28. The apparatus of claim 23 wherein the incipient degradation may be caused by at least one of erosion, corrosion, sintering, cracking, spallation, bond delamination, impact damage due to an object, air cooling starvation, air cooling blockage, and overcooling.

* * * * *